(12) United States Patent
Hashimoto et al.

(10) Patent No.: US 10,722,313 B2
(45) Date of Patent: Jul. 28, 2020

(54) ROBOT SYSTEM AND METHOD OF OPERATING THE SAME

(71) Applicant: KAWASAKI JUKOGYO KABUSHIKI KAISHA, Kobe-shi, Hyogo (JP)

(72) Inventors: Yasuhiko Hashimoto, Kobe (JP); Masayuki Kamon, Akashi (JP); Shigetsugu Tanaka, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 362 days.

(21) Appl. No.: 15/755,324

(22) PCT Filed: May 27, 2016

(86) PCT No.: PCT/JP2016/002588
§ 371 (c)(1),
(2) Date: Feb. 26, 2018

(87) PCT Pub. No.: WO2017/033361
PCT Pub. Date: Mar. 2, 2017

(65) Prior Publication Data
US 2018/0257218 A1 Sep. 13, 2018

(30) Foreign Application Priority Data
Aug. 25, 2015 (JP) ................... 2015-165479

(51) Int. Cl.
*B25J 3/00* (2006.01)
*A61B 34/37* (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ........... A61B 34/37; A61B 34/32; G06T 7/62; G06T 7/70; B23P 19/04; B23P 21/00;
(Continued)

(56) References Cited

U.S. PATENT DOCUMENTS

| 3,893,573 A * | 7/1975 | Fletcher ................. B25J 3/04 414/2 |
| 8,521,331 B2 * | 8/2013 | Itkowitz ................ A61B 34/35 700/264 |

(Continued)

FOREIGN PATENT DOCUMENTS

| JP | 2003-311661 A | 11/2003 |
| JP | 2011-093062 A | 5/2011 |

OTHER PUBLICATIONS

Morooka, Shape Control of Rolling Mills by a Neural and Fuzzy Hybrid Architecture, 1995, IEEE, p. 47-48 (Year: 1995).*
(Continued)

*Primary Examiner* — Mcdieunel Marc
(74) *Attorney, Agent, or Firm* — Oliff PLC

(57) ABSTRACT

A robot system which includes a manipulator, slave arm, an output device, a storage device and a control device. Control device is configured, after a given first process, to output to the output device an inquiry of asking which operating mode among three operating modes of an automatic operation mode, manual operation mode, and hybrid operation mode the slave arm is to be operated in a second process, and execute first operation processing in which, when selected information for instructing the operating mode selected from the three operating modes is inputted, the selected information is stored in the storage device, and second operation processing in which, when the number of times that first selected information is stored in the storage device becomes equal to or more than a first threshold number of times, the (Continued)

selected operating mode is outputted to the output device after the first process is ended.

8 Claims, 10 Drawing Sheets

(51) Int. Cl.
| | |
|---|---|
| *G05B 19/418* | (2006.01) |
| *B23P 19/04* | (2006.01) |
| *B25J 13/00* | (2006.01) |
| *B25J 19/04* | (2006.01) |
| *B25J 9/00* | (2006.01) |
| *B25J 9/16* | (2006.01) |
| *B25J 13/08* | (2006.01) |
| *B25J 13/06* | (2006.01) |
| *B25J 18/00* | (2006.01) |
| *B25J 19/02* | (2006.01) |
| *B25J 3/04* | (2006.01) |
| *B23Q 15/12* | (2006.01) |
| *B25J 13/02* | (2006.01) |
| *B25J 11/00* | (2006.01) |
| *G06F 3/01* | (2006.01) |
| *H04N 5/232* | (2006.01) |
| *H04N 7/18* | (2006.01) |
| *A61B 34/32* | (2016.01) |
| *G06T 7/62* | (2017.01) |
| *G06T 7/70* | (2017.01) |
| *B23P 21/00* | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC . B23Q 15/12; B25J 3/00; B25J 9/0081; B25J 9/0084; B25J 9/0087; B25J 9/1602; B25J 9/1628; B25J 9/1612; B25J 9/163; B25J 9/1633; B25J 9/1646; B25J 9/1653; B25J 9/1664; B25J 9/1669; B25J 9/1674; B25J 9/1682; B25J 9/1689; B25J 9/1697; B25J 11/008; B25J 13/00; B25J 13/003; B25J 13/006; B25J 13/02; B25J 13/025; B25J 13/06; B25J 13/065; B25J 13/08; B25J 13/084; B25J 13/085; B25J 13/087; B25J 13/088; B25J 18/00; B25J 19/023; B25J 19/028; B25J 19/04; G05B 19/4182; G05B 2219/33007; G05B 2219/35464; G05B 2219/37297; G05B 2219/39004; G05B 2219/39102; G05B 2219/39439; G05B 2219/39531; G05B 2219/39533; G05B 2219/40022; G05B 2219/40143; G05B 2219/40145; G05B 2219/40146; G05B 2219/40161; G05B 2219/40162; G05B 2219/40163; G05B 2219/40169; G05B 2219/40182; G05B 2219/40183; G05B 2219/40185; G05B 2219/40195; G05B 2219/40387; G05B 2219/40627; G06F 3/017; H04N 5/23219; H04N 7/181; Y10S 901/02; Y10S 901/03; Y10S 901/08; Y10S 901/09; Y10S 901/10; Y10S 901/27; Y10S 901/41; Y10S 901/46; Y10S 901/47
See application file for complete search history.

(56) References Cited

U.S. PATENT DOCUMENTS

| | | | |
|---|---|---|---|
| 8,942,846 B2* | 1/2015 | Jacobsen | B25J 3/04 700/245 |
| 9,107,684 B2* | 8/2015 | Ma | H04B 5/0037 |
| 9,333,042 B2* | 5/2016 | Diolaiti | A61B 34/37 |
| 9,364,171 B2* | 6/2016 | Harris | A61B 5/150389 |
| 10,123,844 B2* | 11/2018 | Nowlin | B25J 9/1682 |
| 10,486,330 B2* | 11/2019 | Giles | C04B 28/02 |
| 2012/0294696 A1 | 11/2012 | Summer et al. | |
| 2013/0211590 A1 | 8/2013 | Diolaiti et al. | |

OTHER PUBLICATIONS

Harrigan, The Role of Model Based Control in Robotics, 1990, IEEE, p. 1426-1431 (Year: 1990).*
Yokokohji et al., Operation modes for cooperating with autonomous functions in intelligent teleoperation systems, 1993, IEEE, p. 510-515 (Year: 1993).*
Fong et al., Distributed microcomputer control system for advanced teleoperation, 1986, IEEE, p. 987-995 (Year: 1986).*

(56) References Cited

OTHER PUBLICATIONS

Jul. 26, 2016 Search Report issued in International Patent Application No. PCT/JP2016/002588.
Feb. 27, 2018 International Preliminary Report on Patentability issued in International Patent Application No. PCT/JP2016/002588.

* cited by examiner

| OPERATION (PROCESS) ORDER | OPERATING MODE |
|---|---|
| < PROCESS 1 > | AUTOMATIC OPERATION MODE |
| < PROCESS 2 > | SELECTED OPERATING MODE |
| < PROCESS 3 > | HYBRID OPERATION MODE |
| < PROCESS 4 > | MANUAL OPERATION MODE |

FIG. 2

ROBOT SYSTEM AND METHOD OF OPERATING THE SAME

TECHNICAL FIELD

The present disclosure relates to a robot system and a method of operating the same.

BACKGROUND ART

Hand guiding systems for attaching a workpiece to a work target moving on an assembly line are known (e.g., see Patent Document 1).

In the hand guiding system disclosed in Patent Document 1, a robot control device has an automatic mode for automatically controlling a robot and a manual mode for manually controlling the robot with an on-hand operation panel, and it switches to the collaborative mode only for works which require human determination or experience, and other works are carried out in the automatic mode.

REFERENCE DOCUMENT OF CONVENTIONAL ART

Patent Document

[Patent Document 1] JP2011-093062A

DESCRIPTION OF THE DISCLOSURE

Problems to be Solved by the Disclosure

However, in the hand guiding system disclosed in Patent Document 1, the switch from the automatic mode to the collaborative mode is performed by a state display device displaying a switchable state in which the switch to the collaborative mode is possible when the automatic mode is ended, and an operator manipulating an external operation panel based on the display. When the collaborative mode is then ended, it is switched to the automatic mode by the operator manipulating the external operation panel.

As described above, in the hand guiding system disclosed in Patent Document 1, it is required that the operator manipulates the operation panel every time the mode is switched, and a troublesome work is caused. Therefore, there is still a room for improvement in view of reducing the work load on the operator and improving work efficiency.

The present disclosure is for solving the conventional issue and aims to provide a robot system and a method of operating the same, with which a work load on an operator is able to be reduced and work efficiency is able to be improved.

Summary of the Disclosure

In order to solve the conventional issue, a robot system according to the present disclosure includes a manipulator configured to receive a manipulating instruction from an operator, a slave arm configured to perform a series of works comprised of a plurality of processes, an output device, a storage device, and a control device. The control device is configured, after a given first process, to output to the output device an inquiry of asking which operating mode among three operating modes of an automatic operation mode, a manual operation mode, and a hybrid operation mode the slave arm is to be operated in a second process that is the subsequent process to the first process, and execute first operation processing in which, when selected information for instructing the operating mode selected from the three operating modes is inputted from the manipulator, the selected information is stored in the storage device, and second operation processing in which, when the number of times that first selected information indicating the same selected operating mode is stored in the storage device becomes equal to or more than a first threshold number of times, the selected operating mode is outputted to the output device after the first process is ended.

Thus, if the second process is performed in the same operating mode, it becomes unnecessary to manipulate the manipulator to output the selected information after the first process is ended, which allows a work load on the operator to be reduced. Therefore, it is possible to improve work efficiency of the operator.

Further, a method of operating a robot system according to the present disclosure is a method of operating a robot system including a manipulator configured to receive a manipulating instruction from an operator, a slave arm configured to perform a series of works comprised of a plurality of processes, and an output device. The method includes (A) outputting, from the output device after a given first process, an inquiry of asking which operating mode among three operating modes of an automatic operation mode, a manual operation mode, and a hybrid operation mode the slave arm is to be operated in a second process that is the subsequent process to the first process, (B) outputting from the manipulator selected information for instructing the operating mode selected from the three operating modes for the second process, (C) storing in the storage device the selected information outputted by the outputting (B), and (D) outputting, when the number of times that first selected information in which the selected operating mode is the same becomes equal to or more than a first threshold number of times, the selected operating mode from the output device after the first process is ended.

Thus, if the second process is performed in the same operating mode, it becomes unnecessary to manipulate the manipulator to output the selected information after the first process is ended, which allows the work load on the operator to be reduced. Therefore, it is possible to improve the work efficiency of the operator.

Effect of the Disclosure

According to the robot system and the method of operating the same, a work load on an operator is able to be reduced and work efficiency is able to be improved.

BRIEF DESCRIPTION OF DRAWINGS

FIG. 2 is a schematic diagram illustrating one example of operation sequence information stored in a storage device of the robot system illustrated in FIG. 1.

MODES FOR CARRYING OUT THE DISCLOSURE

Figure 1:
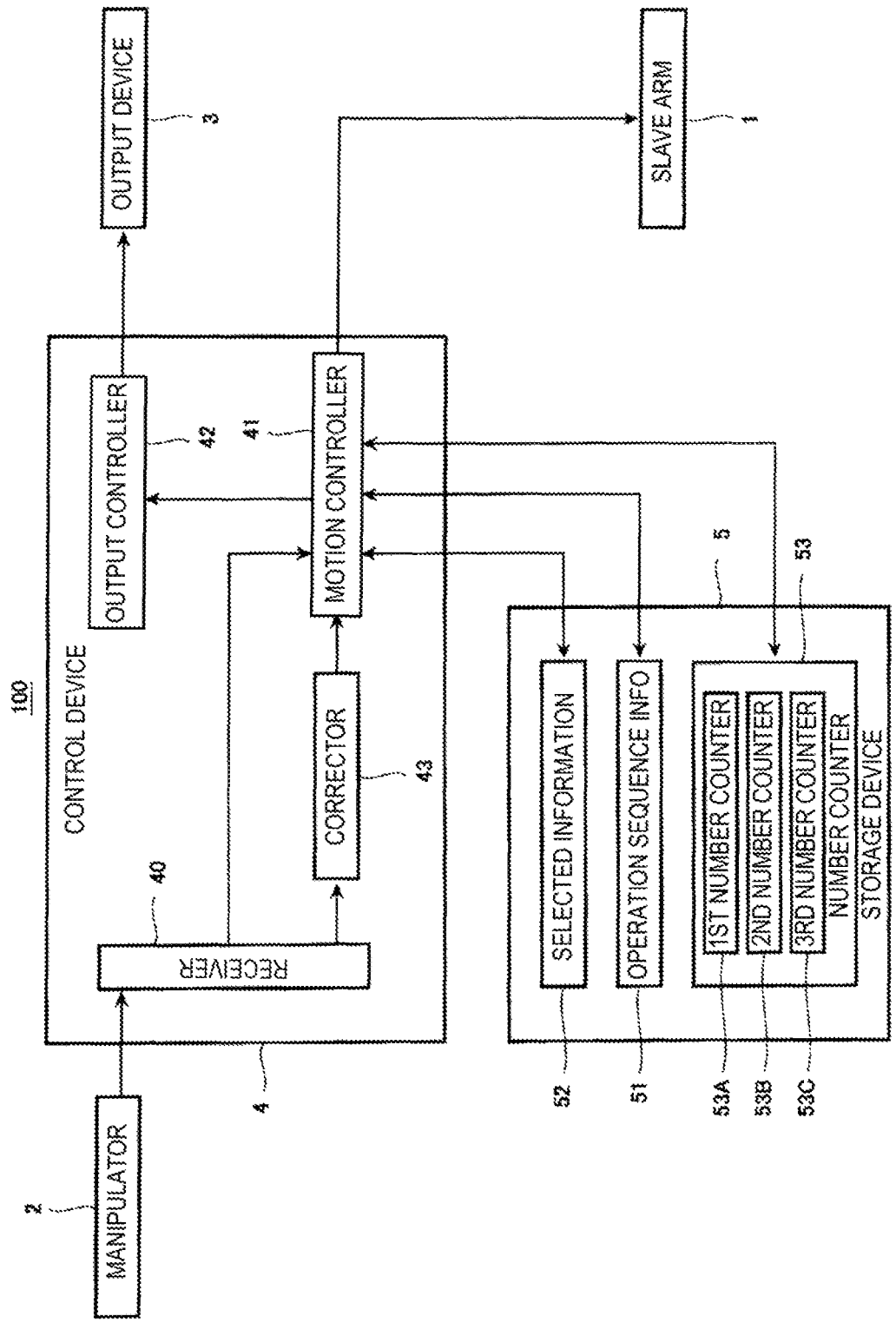
FIG. 1 is a block diagram illustrating a schematic configuration of a robot system according to a first embodiment.

Hereinafter, embodiments of the present disclosure will be described with reference to the drawings. Note that, throughout the drawings, the same reference characters are assigned to the same or corresponding parts and redundant description is omitted. Further, throughout the drawings, elements for describing the present disclosure are selectively illustrated and illustration of the other components may be omitted. Furthermore, the present disclosure is not limited to the following embodiments.

First Embodiment

A robot system according to the first embodiment includes a manipulator which receives a manipulating instruction from an operator, a slave arm which performs a series of works comprised of a plurality of processes, an output device, a storage device, and a control device. The control device is configured, after a given first process, to output to the output device an inquiry of asking which operating mode among three operating modes of an automatic operation mode, a manual operation mode, and a hybrid operation mode the slave arm is to be operated in a second process which is the subsequent process to the first process, and to execute first operation processing in which, when selected information for instructing the operating mode selected from the three operating modes is inputted from the manipulator, the selected information is stored in the storage device, and second operation processing in which, when the number of times that first selected information indicating the same selected operating mode is stored in the storage device becomes equal to or more than a first threshold number of times, the selected operating mode is outputted to the output device after the first process is ended.

Hereinafter, one example of the robot system according to the first embodiment is described with reference to FIGS. 1 to 5.

[Configuration of Robot System]

FIG. 1 is a block diagram illustrating a schematic configuration of a robot system according to the first embodiment.

As illustrated in FIG. 1, the robot system 100 according to the first embodiment includes a slave arm 1, a manipulator 2, an output device 3, a control device 4, and a storage device 5, and it is configured so that the slave arm 1 is operated by an operator operating the manipulator 2.

The slave arm 1 is a robot which is installed in a workspace and performs a series of works comprised of a plurality of processes. Note that the series of works comprised of the plurality of processes may include works, such as assembling of component(s) to a product and painting.

The slave arm 1 according to the first embodiment is an articulated robot, in a line production or a cell production, which is utilized at a production plant where products are produced by assembling electric and/or electronic components etc., is disposed along a workbench provided to the production plant, and is capable of performing at least one of works, such as transferring, assembling or relocating of component(s), and converting the posture, to workpiece(s) on the workbench. Note that the embodiment of the slave arm 1 is not limited to the configuration described above, but may be widely applied to any articulated robots, regardless of a horizontal articulated type or a vertical articulated type.

The manipulator 2 is a device which is installed outside the workspace and receives a manipulating instruction from the operator. Further, as described later, the manipulator 2 is configured, in response to the inquiry of which operating mode the slave arm is to be operated in among the three operating modes of the automatic operation mode, the manual operation mode, and the hybrid operation mode in the second process, to select one of the three operating modes and output the selected operating mode as the selected information. Moreover, the manipulator 2 may be configured so that when the manual operation mode or the hybrid operation mode is ended, it outputs information indicating the end of the operating mode by the operator's manipulation.

The manipulator 2 may be, for example, a master arm, a joystick, or a tablet computer. Note that the manipulator 2 may be separately provided with an input part etc. which inputs a start instruction of a work described later, a notice of completion of the work by a manual operation, etc.

The output device 3 is for outputting information transmitted from the control device 4 and is configured to output the inquiry of which operating mode the slave arm 1 is to be operated in among the three operating modes of the automatic operation mode, the manual operation mode, and the hybrid operation mode (inquiry information).

Further, the output device 3 may be, for example, a display device, such as a monitor, a speaker, a printer, etc. For example, when the output device 3 is constituted by the display device, it displays (outputs) the information transmitted from the control device 4 as an image, for example, letter(s), a painting, a picture, a video, etc. When the output device 3 is constituted by the speaker, it outputs the information transmitted from the control device 4 as sound information. Moreover, when the output device 3 is constituted by the printer, it prints out the information transmitted from the control device 4. Note that the output device 3 is provided at a position where the operator of the manipulator 2 is able to sense the information outputted.

The storage device 5 is a readable and writable recording medium, which stores operation sequence information 51, selected information 52 and a number counter 53 of the robot system 100. Note that, although in the robot system 100 according to the first embodiment, the storage device 5 is provided separately from the control device 4, it may be integrally provided with the control device 4.

The operation sequence information 51 is information relating to an operation sequence which defines the series of works to be performed by the slave arm 1 in the workspace, and includes a program for causing the slave arm 1 to perform an automatic operation. More specifically, the operation sequence information 51 is information where an operation order (process order) and an operating mode of the slave arm 1 (operating mode) are associated with each other.

Note that the operation sequence information 51 also includes an operation flow (not illustrated) of each operating mode.

Here, the operation sequence information 51 will be described in detail with reference to FIG. 2.

FIG. 2 is a schematic diagram illustrating one example of the operation sequence information stored in the storage device of the robot system illustrated in FIG. 1.

As illustrated in FIG. 2, in the first embodiment, according to the operation sequence information 51, the operations of Processes 1 to 4 are executed. In Process 1, the automatic operation mode is executed, and once Process 1 is ended, the inquiry of which operating mode the slave arm 1 is to be operated in among the three operating modes of the automatic operation mode, the manual operation mode, and the hybrid operation mode in Process 2 is performed. Then in Process 2, the operating mode selected by the operator manipulating the manipulator 2 is executed, in Process 3, the hybrid operation mode is executed, and in Process 4, the manual operation mode is executed.

Thus, in the first embodiment, Process 1 constitutes a first process, and Process 2 constitutes a second process. Note that the inquiry of which operating mode the operation is to be performed in among the three operating modes is not limited to the form in which it is performed after Process 1 is ended, but it may be performed after at least one of Processes 1 to 3 is ended, and a form in which it is performed when the respective processes of Processes 1 to 3 are ended may be adopted.

Note that the automatic operation mode means that the slave arm 1 automatically performs the operation according to a preset program. Moreover, the manual operation mode means that the slave arm 1 operates in accordance with the manipulating instruction received from the manipulator 2. The slave arm 1 may be operated to completely follow the manipulating instruction received from the manipulator 2 or the slave arm 1 may be operated while correcting the manipulating instruction received from the manipulator 2 with the preset program (e.g., hand shake correction). Further, the hybrid operation mode means that the operation of the slave arm during the automatic operation is corrected by a manual operation.

The selected information 52 is information on the operating mode selected by the operator from the three operating modes. Further the number counter 53 is for storing the number of times that the operator selects each operating mode for the second process. A first number counter 53A is configured to store the number of times that the automatic operation mode is selected, a second number counter 53B is configured to store the number of times that the manual operation mode is selected, and a third number counter 53C is configured to store the number of times that the hybrid operation mode is selected.

The control device 4 controls the operation of the slave arm 1, and includes a receiver 40, a motion controller 41, an output controller 42, and a corrector 43 as functional blocks. The control device 4 may be comprised of, for example, an arithmetic part (not illustrated), such as a microcontroller, an MPU and a PLC (Programmable Logic Controller), a logic circuit, etc., and a memory part (not illustrated), such as a ROM or a RAM. Moreover, each functional block provided to the control device 4 is implementable by the arithmetic part of the control device 4 reading and executing the program stored in a memory part or the storage device 5.

Note that the control device 4 may not only be in a form comprised of a single control device, but also in a form comprised of a group of control devices in which a plurality of control devices collaborate with each other to execute the control of the slave arm 1 (robot system 100).

The receiver 40 receives an input signal transmitted from the outside of the control device 4. The input signal received by the receiver 40 may be, for example, a signal transmitted from the manipulator 2, a signal transmitted from a manipulating instruction part (not illustrated) other than the manipulator 2, etc.

When the receiver 40 receives the manipulating instruction from the manipulator 2 as the input signal, the motion controller 41 determines the operating mode of the process which the slave arm 1 carries out in the series of works by using the manipulating instruction as a trigger. The motion controller 41 is capable of performing the determination of the operating mode of the process which the slave arm 1 carries out next, with reference to the operation sequence information 51 stored in the storage device 5. Once the motion controller 41 determines the operating mode, it controls the slave arm 1 so that the slave arm 1 is operated in the determined operating mode.

For example, if the motion controller 41 determines that the slave arm 1 is to be automatically operated, it reads the operation sequence information 51, and controls the slave arm 1 to perform the operation defined by the program contained in the operation sequence information 51.

On the other hand, if the motion controller 41 determines that the slave arm 1 is to be manually operated, it controls the slave arm 1 to perform the operation based on the manipulating instruction received from the manipulator 2 by the receiver 40.

Further, if the motion controller 41 determines that the slave arm 1 is to be operated in hybrid, it reads the operation sequence information 51 and performs the operation defined by the program contained in the operation sequence information 51, and when the receiver 40 receives a correctable instructing signal as an input signal from the manipulator 2 during the operation of the slave arm 1 by the automatic operation, the operation of the slave arm 1 by the automatic operation is corrected to operation following the correctable instructing signal from the manipulator 2. Then, when the output of the correcting instruction signal from the manipulator 2 is stopped and the receiver 40 stops receiving the correcting instruction signal, or when the receiver 40 receives an instruction for resuming the automatic operation of the slave arm 1 from the manipulator 2, the motion controller 41 resumes the automatic operation of the slave arm 1.

Note that, when the slave arm 1 is operated in the automatic operation mode, once the automatic operation mode of the slave arm 1 is ended, the motion controller 41 may transmit information indicating that the end of the automatic operation mode to the output controller 42. Therefore, by the output controller 42 outputting the information indicating the end of the automatic operation mode to the output device 3 for the operator, the operator is able to understand that the automatic operation mode is ended.

Further, after the first process is ended, the motion controller 41 outputs the inquiry of which operating mode the slave arm 1 is to be operated in among the three operating modes of the automatic operation mode, the manual operation mode, and the hybrid operation mode (inquiry information) to the output controller 42.

Additionally, the motion controller 41 acquires the selected information outputted from the manipulator 2 via the receiver 40. Moreover, the motion controller 41 stores the acquired selected information in the selected information 52 of the storage device 5 and updates the number counter 53 for the selected operating mode. The update of the number counter 53 is performed, for example, when the operator selects the automatic operation mode, by adding 1 to the first number counter 53A of the number counter 53. Similarly, when the operator selects the manual operation mode, 1 is added to the second number counter 53B, and when the hybrid operation mode is selected, 1 is added to the third number counter 53C.

Then, the motion controller 41 sets the selected information relating to the most selected operating mode among the respective operating modes from the number counter 53 as the first selected information for the second process, and stores it in the selected information 52 of the storage device 5. Further, when the first selected information is selected equal to or more than the preset first threshold number of times, the motion controller 41 outputs to the output controller 42 the operating mode stored as the first selected information after the first process is ended.

The output controller 42 controls the output device 3 to output information to be notified to the operator etc. For example, when the output controller 42 receives the information indicating the start of the automatic operation from the motion controller 41, or when it receives one of the information indicating the start of the manual operation from the manipulator 2 via the motion controller 41 and the receiver 40 and, if it is during the hybrid operation of the slave arm 1, the input signal indicating the correcting instruction from the manipulator 2 via the motion controller 41 and the receiver 40, it may control the output device 3 to output this information.

Furthermore, when the output controller 42 receives the information indicating the end of the automatic operation from the motion controller 41, or when it receives one of the information indicating the end of the manual operation and the information indicating the end of the hybrid operation from the manipulator 2 via the motion controller 41 and the receiver 40, it may control the output device 3 to output this information.

Further, when the output controller 42 receives the inquiry information from the motion controller 41, it controls the output device 3 to output the information. Thus, the operator is able to select which operating mode the slave arm 1 is to be operated in among the three operating modes, and manipulate the manipulator 2 to output the selected information to the receiver 40 of the control device 4.

When the receiver 40 receives the input signal indicating the correcting instruction during the hybrid operation of the slave arm 1, the corrector 43 instructs the motion controller 41 to correct the operation of the slave arm 1. Specifically, when the receiver 40 receives the correcting instruction signal as the input signal from the manipulator 2 during the hybrid operation of the slave arm 1, the corrector 43 instructs the motion controller 41 to correct the operation of the slave arm 1 in the automatic operation to the operation according to the correcting instruction signal from the manipulator 2. Note that, in response to the instruction from the corrector 43, the motion controller 41 controls the slave arm 1 to reflect the correcting instruction from the manipulator 2 on the operation.

[Operation and Effect of Robot System]

Next, operation and effect of the robot system 100 according to the first embodiment are described with reference to FIGS. 1 to 5. Note that since the operation of performing the series of works by the operator manipulating the manipulator 2 to operate the slave arm 1 is executed similar to a known robot system, detailed description thereof is omitted. Moreover, the following operation is executed by the arithmetic part of the control device 4 reading the program stored in the memory part or the storage device 5.

Figure 3:
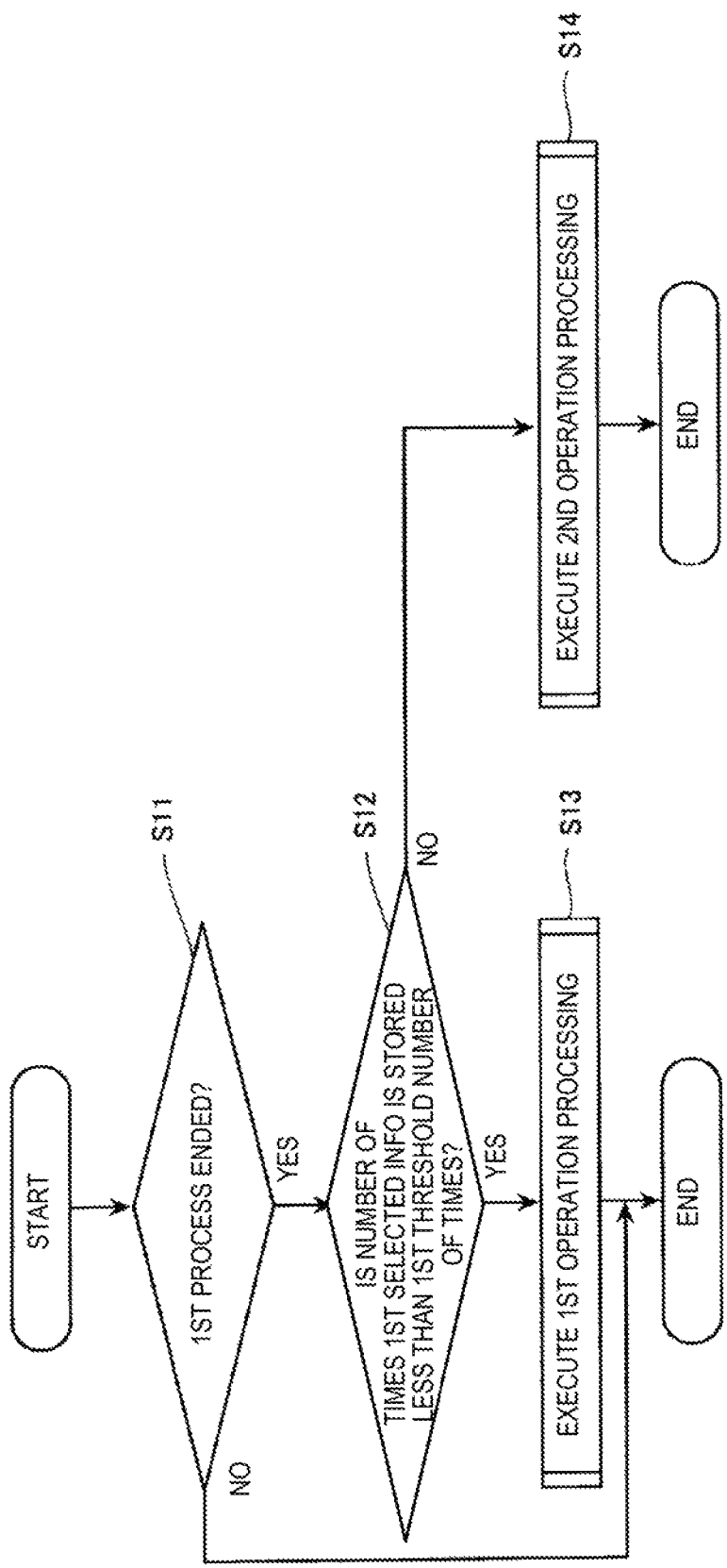
FIG. 3 is a flowchart illustrating one example of operation of the robot system according to the first embodiment.

FIG. 3 is a flowchart illustrating one example of operation of the robot system according to the first embodiment.

As illustrated in FIG. 3, the control device 4 determines whether the first process (Process 1 in the first embodiment) is ended (Step S11). Specifically, the motion controller 41 of the control device 4 determines whether the automatic operation is ended or whether one of the information indicating the end of the manual operation and the information indicating the end of the hybrid operation is received from the manipulator 2 via the receiver 40. Note that in the first embodiment, since Process 1 is the operation in the automatic operation mode, the motion controller 41 determines whether the automatic operation is ended.

If the motion controller 41 of the control device 4 determines that the automatic operation is not ended or one of the information indicating the end of the manual operation and the information indicating the end of the hybrid operation is not received from the manipulator 2 via the receiver 40 (No at Step S11), it ends this program. Note that, when the control device 4 ends this program, it again executes this program, for example, after 50 msec.

On the other hand, if the motion controller 41 of the control device 4 determines that the automatic operation is ended or one of the information indicating the end of the manual operation and the information indicating the end of the hybrid operation is received from the manipulator 2 via the receiver 40 (Yes at Step S11), the processing at S12 is executed.

At Step S12, the control device 4 determines whether the number of times that the first selected information for the second process (here, Process 2) is stored is less than the first threshold number of times. Specifically, the motion controller 41 of the control device 4 acquires the number of times that the first selected information is stored, from the number counter 53 of the storage device 5.

For example, when the most selected operating mode for the second process is the automatic operation, the motion controller 41 acquires the number of times stored, from the first number counter 53A. Similarly, when the most selected operating mode is the manual operation mode, the motion controller 41 acquires the number from the second number counter 53B, and when the most selected operating mode is the hybrid operation mode, the motion controller 41 acquires the number from the third number counter 53C.

If the motion controller 41 determines that the number acquired from the number counter 53 is less than the first threshold number of times (Yes at Step S12), the first operation processing is executed (Step S13) and it ends this program. On the other hand, if the motion controller 41 determines that the number acquired from the number counter 53 is not less than the first threshold number of times (No at Step S12), the second operation processing is executed (Step S14) and it ends this program.

Here, the first threshold number of times may be arbitrarily set, and is suitably set based on the skill, the proficiency level on the slave arm 1, etc., of the operator of the manipulator 2, for example, it may be five times, ten times, or fifteen times. Further, the first threshold number of times may be the number of times that it is selected consecutively, or a total number of times selected.

Next, the first operation processing will be described in detail with reference to FIG. 4.

Figure 4:
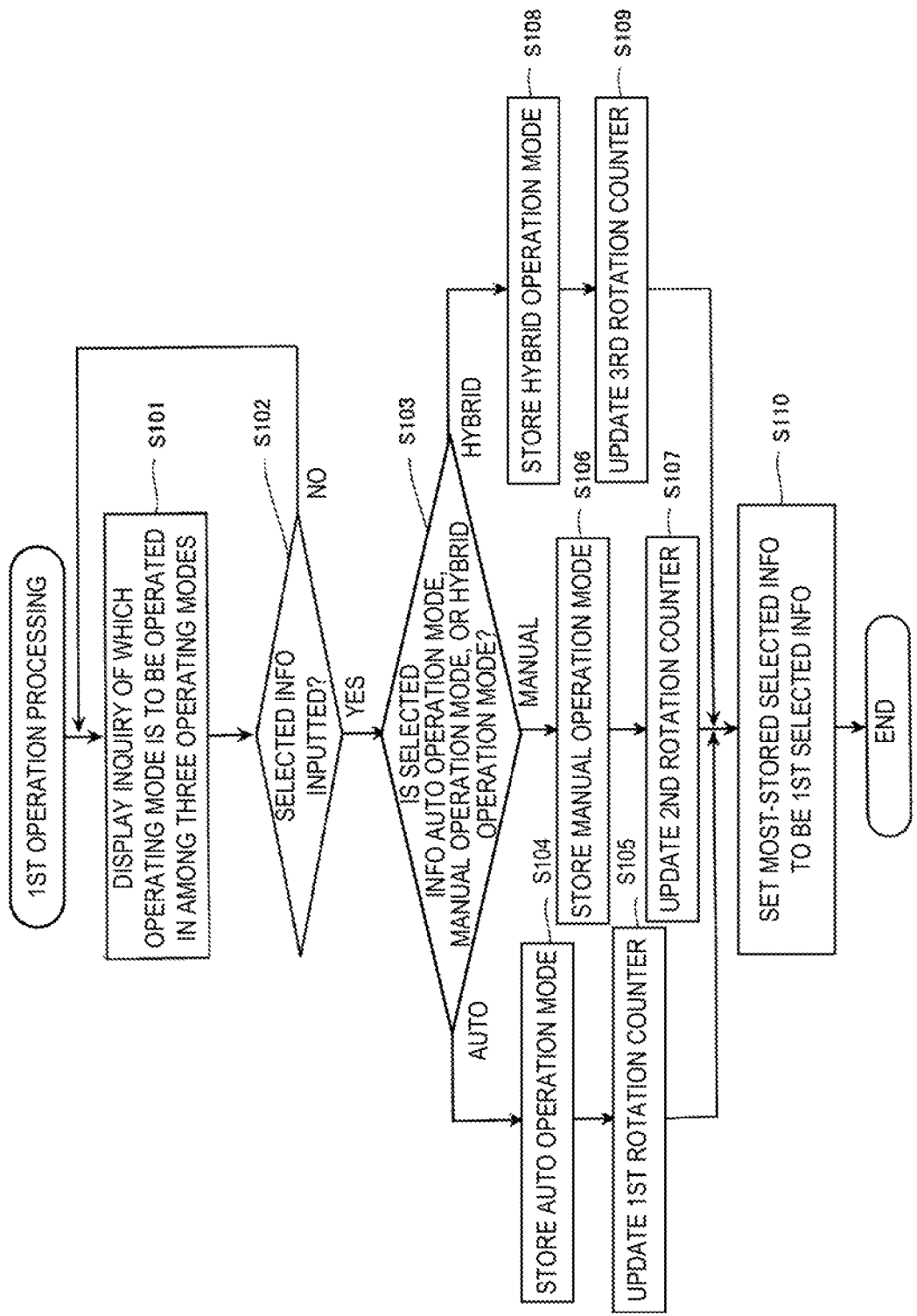
FIG. 4 is a flowchart illustrating one example of specific processing of first operation processing illustrated in FIG. 3.

FIG. 4 is a flowchart illustrating one example of specific processing of the first operation processing illustrated in FIG. 3.

As illustrated in FIG. 4, the control device 4 displays (outputs) the inquiry of which operating mode the slave arm 1 is to be operated in among the three operating modes of the automatic operation mode, the manual operation mode, and the hybrid operation mode (inquiry information) (Step S101). Specifically, the motion controller 41 of the control device 4 outputs the inquiry information to the output device 3 via the output controller 42. Then, by acquiring the inquiry information, the output device 3 displays for the operator the inquiry of which operating mode to operate in among the three operating modes. In response to this, the operator selects which operating mode to operate in among the three operating modes, and manipulates the manipulator 2 to output the selected operating mode as the selected information.

Next, the motion controller 41 of the control device 4 determines whether the selected information is inputted to the receiver 40 from the manipulator 2 (Step S102). If the motion controller 41 determines that the selected information is not inputted from the manipulator 2 to the receiver 40 (No at Step S102), the motion controller 41 returns to Step S101 to repeat S101 and S102 until the selected information is inputted from the manipulator 2 to the receiver 40. On the other hand, if the motion controller 41 determines that the selected information is inputted from the manipulator 2 to the receiver 40 (Yes at Step S102), the motion controller 41 proceeds to Step S103.

At Step S103, the motion controller 41 of the control device 4 determines which operating mode the selected information inputted from the manipulator 2 via the receiver 40 is among the automatic operation mode, the manual operation mode, and the hybrid operation mode.

If the motion controller 41 determines that the selected information indicates the automatic operation mode at Step S103, it causes the selected information 52 of the storage device 5 to store the automatic operation mode (Step S104), updates the first number counter 53A of the number counter 53 (Step S105), and proceeds to Step S110. Further, if the motion controller 41 determines that the selected information indicates the manual operation mode at Step S103, the motion controller 41 causes the selected information 52 of the storage device 5 to store the manual operation mode (Step S106), updates the second number counter 53B (Step S107), and proceeds to Step S110. Furthermore, at Step S103, if the motion controller 41 determines that the selected information indicates the hybrid operation mode, it causes the selected information 52 of the storage device 5 to store the hybrid operation mode (Step S108), updates the third number counter 53C (Step S109), and proceeds to Step S110.

At Step S110, the motion controller 41 of the control device 4 acquires the selected numbers of times of the respective operating modes from the number counter 53 of the storing device 5, sets the selected information which is stored the most to be the first selected information, causes the selected information 52 to store the first selected information, and ends this program. Note that, after the motion controller 41 of the control device 4 determines which operating mode it is at Step S104, and then executes the second process in this operating mode.

Next, the second operation processing will be described in detail with reference to FIG. 5. Note that, as described above, the second operation processing is processing executed when the first selected information is selected and the number of times stored in the number counter 53 is equal to or more than the first threshold number of times.

Figure 5:
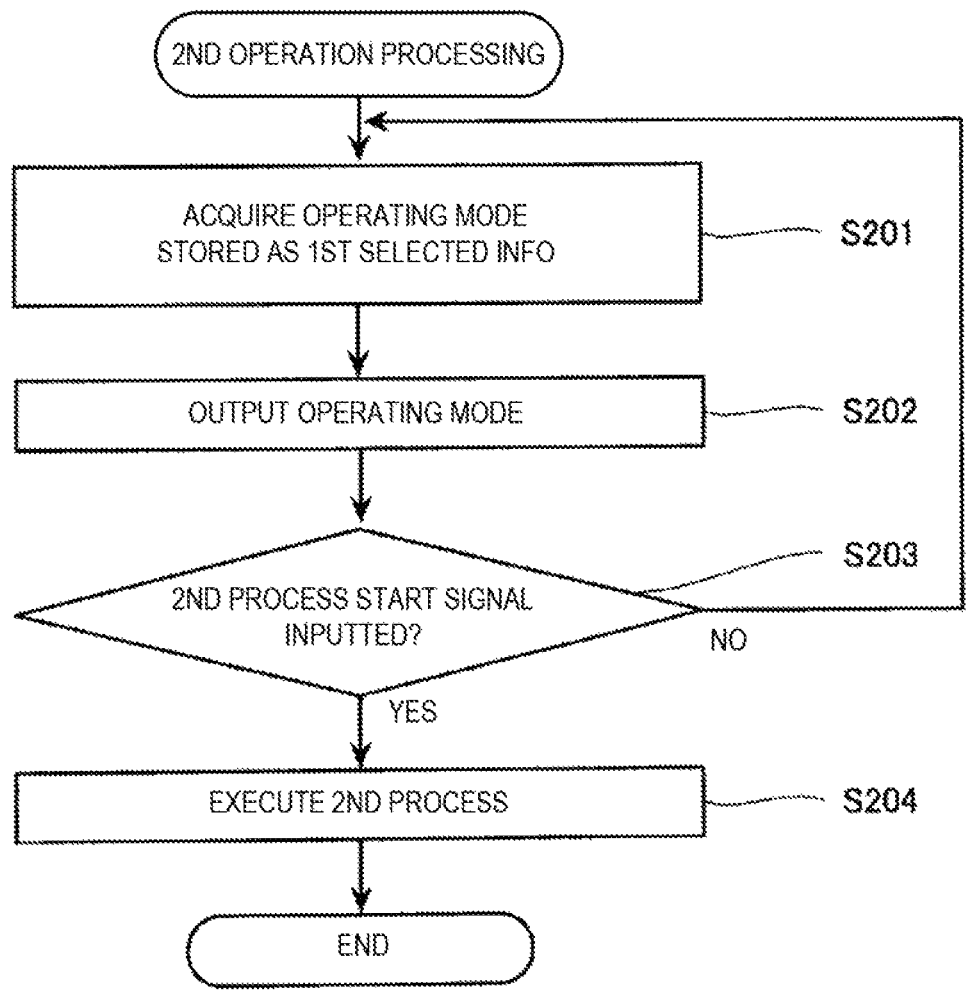
FIG. 5 is a flowchart illustrating one example of specific processing of second operation processing illustrated in FIG. 3.

FIG. 5 is a flowchart illustrating one example of specific processing of the second operation processing illustrated in FIG. 3.

As illustrated in FIG. 5, the motion controller 41 of the control device 4 acquires the operating mode stored as the first selected information from the selected information 52 of the storage device 5 (Step S201). For example, if the automatic operation mode is stored as the first selected information in the selected information 52, the motion controller 41 acquires the automatic operation mode. Similarly, if the manual operation mode is stored as the first selected information in the selected information 52, the motion controller 41 acquires the manual operation mode, and if the hybrid operation mode is stored as the first selected information, the motion controller 41 acquires the hybrid operation mode.

Next, the motion controller 41 of the control device 4 outputs the operating mode acquired at Step S201 to the output device 3 via the output controller 42 (Step S202). Thus, the operator is able to understand in which operating mode the slave arm 1 is to be operated in the second process. Additionally, it becomes unnecessary for the operator to select which operating mode to operate in among the three operating modes, and manipulate the manipulator 2 to output the selected operating mode as the selected information, which allows the work load on the operator to be reduced.

Next, the motion controller 41 of the control device 4 determines whether a start signal for starting the second process is inputted from the manipulator 2 via the receiver 40 by the operator manipulating the manipulator 2 (Step S203).

If the motion controller 41 of the control device 4 determines that the start signal for starting the second process is not inputted from the manipulator 2 via the receiver 40 (No at Step S203), it returns to Step S201 to repeat S201 to S203 until the start signal for starting the second process is inputted.

On the other hand, if the motion controller 41 of the control device 4 determines that the start signal for starting the second process is inputted from the manipulator 2 via the receiver 40 (Yes at Step S203), it executes the second process in the operating mode acquired at S201 (Step S204) and ends this program.

In the robot system 100 according to the first embodiment configured as described above, when the given first process is ended, the inquiry of which operating mode the slave arm 1 is to be operated in among the three operating modes of the automatic operation mode, the manual operation mode, and the hybrid operation mode is displayed on the output device 3. Therefore, it is possible to prompt the operator for the manipulation of the second process.

Further in the robot system 100 according to the first embodiment, when the operator selects the same operating mode for the second process, the selected operating mode and the number of times selected are stored, and after the number of times selected reaches equal to or more than the first threshold number of times, when the first process is ended, the selected operating mode is displayed on the output device 3.

Thus, the operator is able to understand in which operating mode the slave arm 1 is to be operated in the second process. Additionally, it becomes unnecessary for the operator to select which operating mode to operate in among the three operating modes, and manipulate the manipulator 2 to output the selected operating mode as the selected information, which allows the work load on the operator to be reduced. Therefore, it is possible to improve the work efficiency of the operator.

Second Embodiment

A robot system according to a second embodiment is configured so that in the robot system according to the first embodiment, the storage device stores operation sequence information which is information relating to an operation sequence defining a series of works performed by the slave arm, and when the first process is the automatic operation mode and the selected operating mode for the second process is the automatic operation mode, once the number of times that the first selected information is stored in the storage device becomes equal to or more than a second threshold number of times, the control device executes third operation processing in which the operation sequence information is corrected so that the slave arm is operated in the automatic operation mode in the first and second processes.

Further, in the robot system according to the second embodiment, in the third operation processing, the control device may correct the operation sequence information so as to process the first process and the second process as a single process.

Moreover, in the robot system according to the second embodiment, the second threshold number of times may be lower than the first threshold number of times.

Hereinafter, one example of the robot system according to the second embodiment is described with reference to FIGS. 6 to 10. Note that, since the robot system according to the second embodiment has a similar configuration to the robot system 100 according to the first embodiment, detailed description of the configuration thereof is omitted.

[Operation and Effect of Robot System]

Although the operation of the robot system 100 according to the second embodiment is basically the same as the operation of the robot system 100 according to the first embodiment, it is different in that the first process and the second process are performed in the automatic operation mode and, when the number of times that the first selected information is stored becomes equal to or more than the second threshold, the third operation processing is executed. Hereinafter, this is described in detail with reference to FIG. 6.

Note that in the following description, the operation sequence information 51 stored in the storage device 5 of the robot system 100 according to the second embodiment is the same as the operation sequence information 51 illustrated in FIG. 2.

Figure 6:
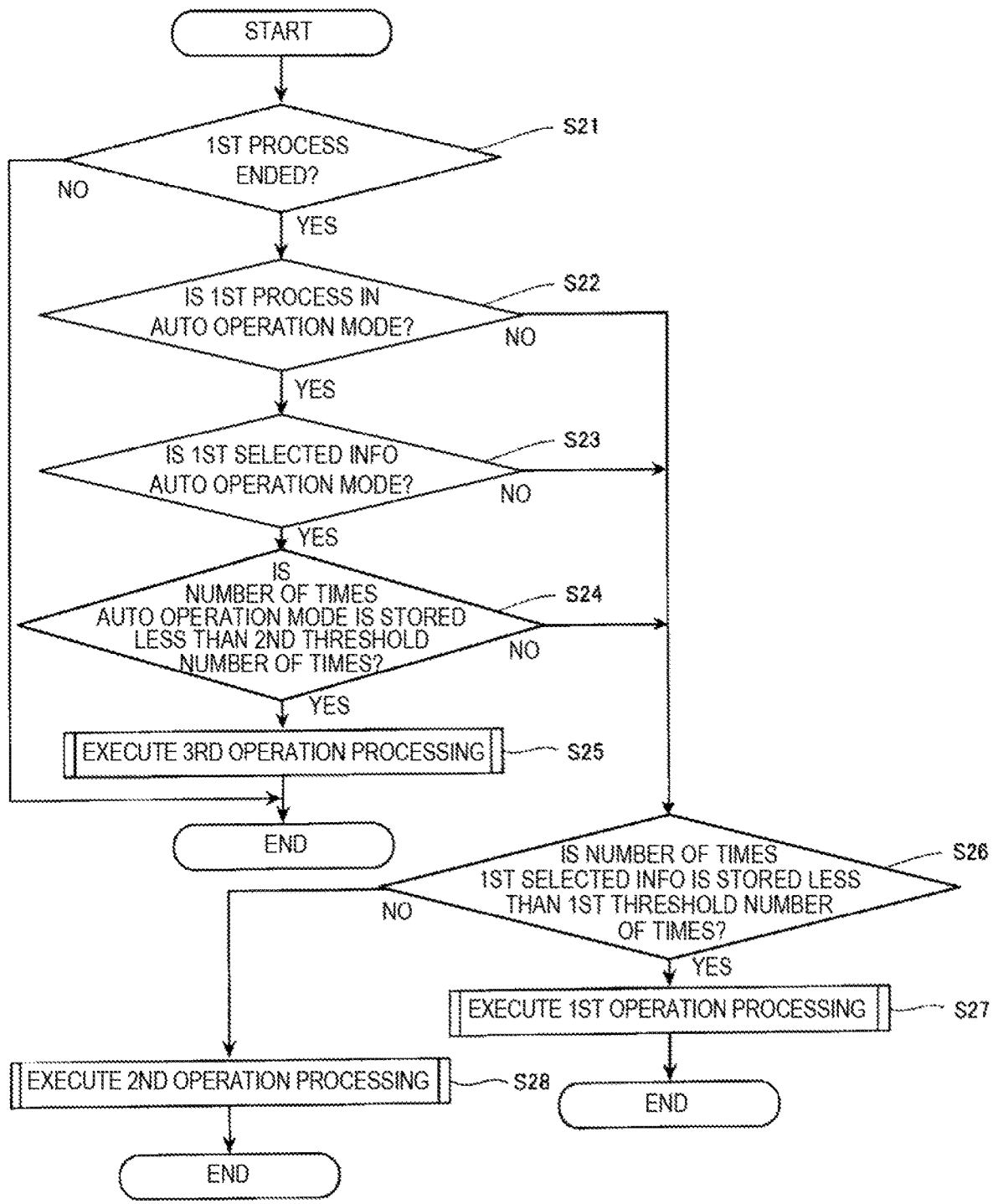
FIG. 6 is a flowchart illustrating one example of operation of a robot system according to a second embodiment.

FIG. 6 is a flowchart illustrating one example of operation of the robot system according to the second embodiment.

As illustrated in FIG. 6, the control device 4 determines whether the first process (Process 1 in the second embodiment) is ended (Step S21). Specifically, the motion controller 41 of the control device 4 determines whether the automatic operation is ended or one of the information indicating the end of the manual operation and the information indicating the end of the hybrid operation is received from the manipulator 2 via the receiver 40. Note that in the second embodiment, since Process 1 is the operation in the automatic operation mode, the motion controller 41 determines whether the automatic operation is ended.

If the motion controller 41 of the control device 4 determines that the automatic operation is not ended or one of the information indicating the end of the manual operation and the information indicating the end of the hybrid operation is not received from the manipulator 2 via the receiver 40 (No at Step S21), it ends this program. Note that, when the control device 4 ends this program, it again executes this program, for example, after 50 msec.

On the other hand, if the motion controller 41 of the control device 4 determines that the automatic operation is ended or one of the information indicating the end of the manual operation and the information indicating the end of the hybrid operation is received from the manipulator 2 via the receiver 40 (Yes at Step S21), the processing at S22 is executed.

At Step S22, the control device 4 determines whether the first process is the automatic operation mode. Specifically, the motion controller 41 of the control device 4 acquires the operation mode of the first process (here, Process 1) from the operation sequence information 51 of the storage device 5 and determines whether the acquired operation mode is the automatic operation mode.

If the motion controller 41 of the control device 4 determines that the first process is not the automatic operation mode (No at Step S22), the motion controller 41 proceeds to Step S26. Note that Step S26 will be described later. On the other hand, if the motion controller 41 of the control device 4 determines that the first process is the automatic operation mode (Yes at Step S22), the motion controller 41 proceeds to Step S23.

At Step S23, the control device 4 determines whether the first selected information which is selected for the second process is the automatic operation mode. Specifically, the motion controller 41 of the control device 4 acquires the operation mode of the second process (here, Process 2) from the selected information 52 of the storage device 5 and determines whether the acquired operation mode is the automatic operation mode.

If the motion controller 41 of the control device 4 determines that the first selected information is not the automatic operation mode (No at Step S23), the motion controller 41 proceeds to Step S26. If the motion controller 41 of the control device 4 determines that the first selected information is the automatic operation mode (Yes at Step S23), the motion controller 41 proceeds to Step S24.

At Step S24, the control device 4 determines whether the number of times that the automatic operation mode which is the first selected information is stored is equal to or more than the second threshold number of times. Specifically, the motion controller 41 of the control device 4 acquires from the first number counter 53A of the storage device 5 the number of times that the automatic operation mode is stored, and determines whether the acquired number of times is equal to or more than the second threshold number of times.

Here, the second threshold number of times may be arbitrarily set, and is suitably set based on the skill, the proficiency level on the slave arm 1, etc., of the operator of the manipulator 2. Further, the second threshold number of times may be lower than the first threshold number of times and it may be, for example, three times, five times, seven times, or ten times.

Further, the second threshold number of times may be the number of times that it is selected consecutively, or a total number of times selected. For example, the motion controller 41 of the control device 4 may determine that it is equal to or more than the second threshold number of times when the automatic operation mode is selected twice consecutively for the second process.

If the motion controller 41 of the control device 4 determines that the number of times that the automatic operation mode is stored is not equal to or more than the second threshold number of times (No at Step S24), the motion controller 41 proceeds to Step S26. At Step S26, similar to the robot system 100 according to the first embodiment, the control device 4 determines whether the number of times that the first selected information is stored for the second process is less than the first threshold number of times.

Specifically, the motion controller 41 of the control device 4 acquires from the number counter 53 of the storage device 5 the number of times that the first selected information is stored and if it determines that the number acquired from the number counter 53 is less than the first threshold number of times (Yes at Step S26), the first operation processing is executed (Step S27) and it ends this program. On the other hand, if the motion controller 41 determines that the number acquired from the number counter 53 is not less than the first threshold number of times (No at Step S26), the second operation processing is executed (Step S28) and it ends this program.

On the other hand, if the motion controller 41 of the control device 4 determines that the number of times that the automatic operation mode is stored is equal to or more than the second threshold number of times (Yes at Step S24), the third operation processing is executed (Step S25) and it ends this program.

Next, the third operation processing will be described in detail with reference to FIGS. 7 to 10.

Figure 7:
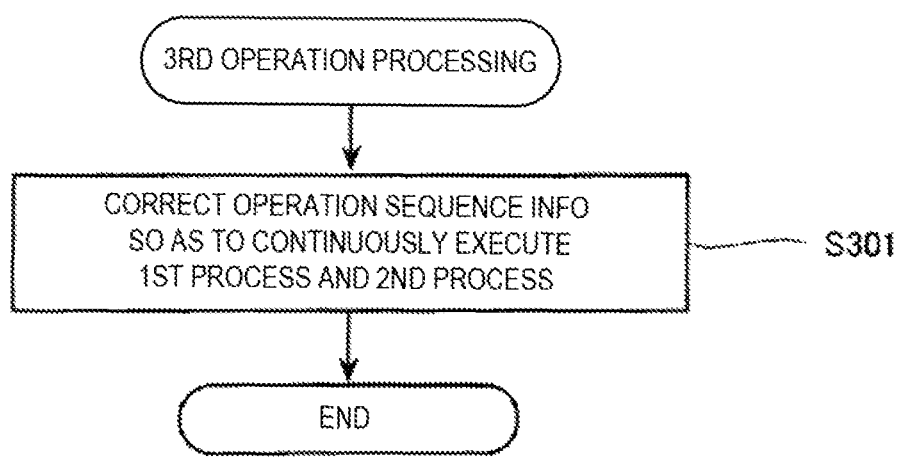
FIG. 7 is a flowchart illustrating one example of specific processing of third operation processing illustrated in FIG. 6.
Figure 8:
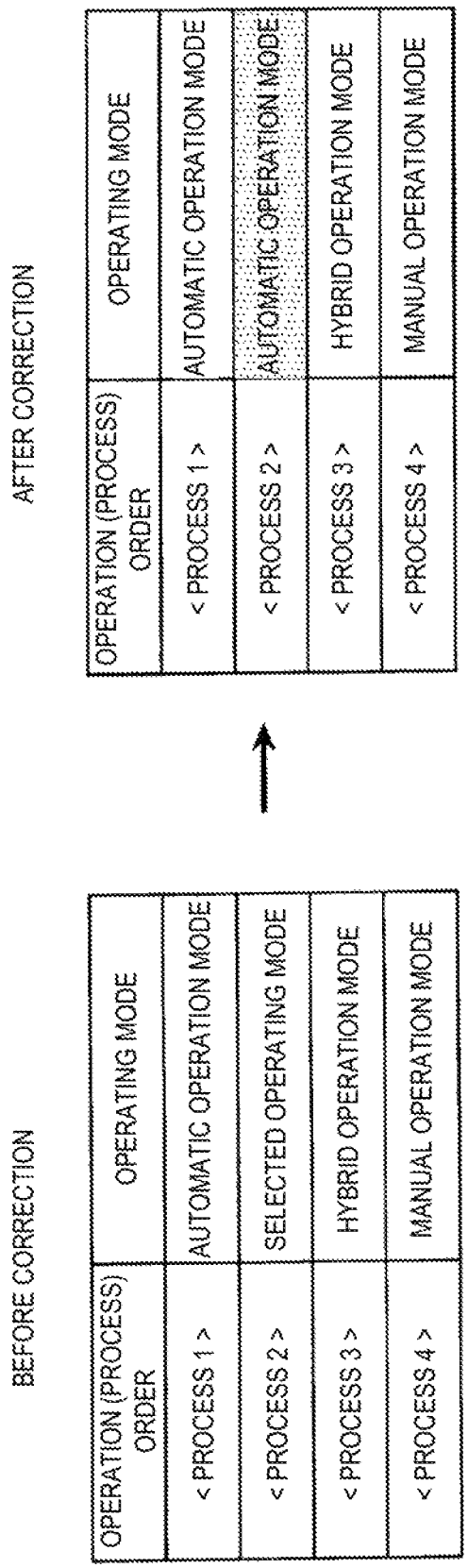
FIG. 8 is a schematic diagram illustrating operation sequence information before corrected and operation sequence information after corrected by the third operation processing illustrated in FIG. 7.
Figure 9:
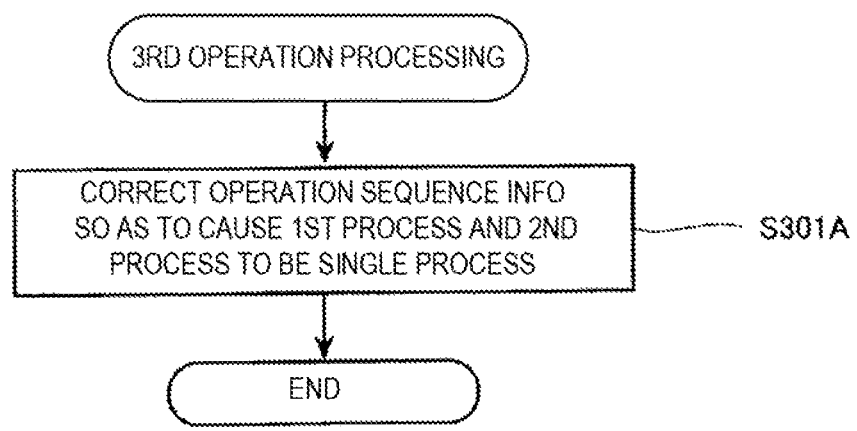
FIG. 9 is a flowchart illustrating another example of specific processing of the third operation processing illustrated in FIG. 6.
Figure 10:
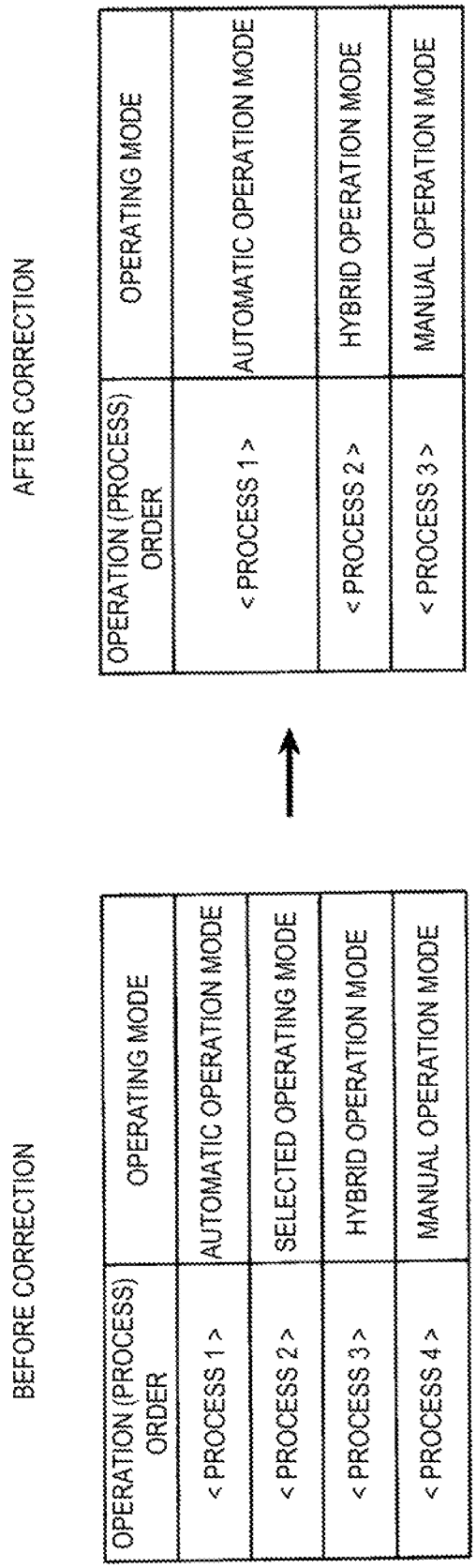
FIG. 10 is a schematic diagram illustrating operation sequence information before corrected and operation sequence information after corrected by the third operation processing illustrated in FIG. 9.

FIG. 7 is a flowchart illustrating one example of specific processing of the third operation processing illustrated in FIG. 6. FIG. 8 is a schematic diagram illustrating operation sequence information before corrected and operation sequence information after corrected by the third operation processing illustrated in FIG. 7. Further, FIG. 9 is a flowchart illustrating another example of specific processing of the third operation processing illustrated in FIG. 6. FIG. 10 is a schematic diagram illustrating operation sequence information before corrected and operation sequence information after corrected by the third operation processing illustrated in FIG. 9.

As illustrated in FIG. 7, the motion controller 41 of the control device 4 corrects the operation sequence information 51 so as to continuously execute the first process and the second process (Step S301), and ends this program. Specifically, as illustrated in FIG. 8, the motion controller 41 corrects the operating mode of Process 2 of the operation sequence information 51 to the automatic operation mode, and when the operation sequence information 51 is executed, once the automatic operation mode of Process 1 is ended, the automatic operation mode of Process 2 is executed subsequently.

Note that when the automatic operation mode of Process 1 is ended, the motion controller 41 may cause the output device 3 to output information on the end of automatic operation via the output controller 42, or it may execute the automatic operation mode of Process 2 without the output. Further, the motion controller 41 may be configured, when the automatic operation mode of Process 1 is ended, to execute the second process even without the operator manipulating the manipulator 2 to output the start signal of the automatic operation mode of the second process.

Moreover, as illustrated in FIG. 9, the motion controller 41 of the control device 4 may correct the operation sequence information 51 so as to cause the first process and the second process to be a single process (Step S301A), and end this program. Specifically, as illustrated in FIG. 10, the motion controller 41 may integrate Processes 1 and 2 into Process 1 and execute a correction to bring up Process 3 and Process 4 to Process 2 and Process 3, respectively. Thus, when executing the operation sequence information 51 corrected by the motion controller 41, Process 1 before the correction and Process 2 are executed consecutively.

Even with the robot system 100 according to the second embodiment configured as above, similar operations and effects to those of the robot system according to the first embodiment are obtained.

Further, in the robot system 100 according to the second embodiment, the first process and the second process are performed in the automatic operation mode and, when the number of times that the first selected information is stored is equal to or more than the second threshold, the first process and the second process are executed consecutively. Thus, since the second process is executed even without the operator manipulating the manipulator 2 to output the start signal of the automatic operation mode of the second process, compared with the robot system 100 according to the first embodiment, it is possible to further reduce the work load on the operator. Therefore, it is possible to further improve the work efficiency of the operator.

It is apparent for a person skilled in the art that many improvements or other embodiments of the present disclosure are possible from the above description. Therefore, the above description is to be interpreted only as illustration, and it is provided in order to teach a person skilled in the art the best mode in which the present disclosure is implemented. Details of the structures and/or functions of the present disclosure may be substantially changed without departing from the spirit of the present disclosure.

INDUSTRIAL APPLICABILITY

Since the robot system of the present disclosure and the method of operating the same are capable of reducing the work load on the operator and improving the work efficiency, they are useful in the field of industrial robots.

DESCRIPTION OF REFERENCE CHARACTERS

1 Slave Arm
2 Manipulator
3 Output Device
4 Control Device
5 Storage Device
40 Receiver
41 Motion Controller
42 Output Controller
43 Corrector
51 Operation Sequence Information
52 Selected information
53 Number Counter
53A First Number Counter
53B Second Number Counter
53C Third Number Counter
100 Robot System

The invention claimed is:

1. A robot system, comprising:
   a manipulator configured to receive a manipulating instruction from an operator;
   a slave arm configured to perform a series of works comprised of a plurality of processes;
   an output device;
   a storage device; and
   a control device,
   wherein the control device is configured, after a given first process, to output to the output device an inquiry of asking which operating mode among three operating modes of an automatic operation mode, a manual operation mode, and a hybrid operation mode the slave arm is to be operated in a second process that is the subsequent process to the first process, and execute first operation processing in which, when selected information for instructing the operating mode selected from the three operating modes is inputted from the manipulator, the selected information is stored in the storage device, and second operation processing in which, when the number of times that first selected information indicating the same selected operating mode is stored in the storage device becomes equal to or more than a first threshold number of times, the selected operating mode is outputted to the output device after the first process is ended.

2. The robot system of claim 1, wherein the storage device stores operation sequence information that is information relating to an operation sequence in which the series of works performed by the slave arm are defined, and wherein, when the first process is the automatic operation mode and the selected operating mode for the second process is the automatic operating mode, once the number of times that the first selected information is stored in the storage device becomes equal to or more than a second threshold number of times, the control device is configured to execute third operation processing in which the operation sequence information is corrected so that the slave arm is operated in the automatic operation mode for the first and second processes.

3. The robot system of claim 2, wherein in the third operation processing, the control device corrects the operation sequence information so that the first process and the second process are processed as a single process.

4. The robot system of claim 2, wherein the second threshold number of times is lower than the first threshold number of times.

5. A method of operating a robot system including a manipulator configured to receive a manipulating instruction from an operator, a slave arm configured to perform a series of works comprised of a plurality of processes, and an output device, comprising:

(A) outputting, from the output device after a given first process, an inquiry of asking which operating mode among three operating modes of an automatic operation mode, a manual operation mode, and a hybrid operation mode the slave arm is to be operated in a second process that is the subsequent process to the first process;

(B) outputting from the manipulator selected information for instructing the operating mode selected from the three operating modes for the second process;

(C) storing in a storage device the selected information outputted by the outputting (B); and (D) outputting, when the number of times that first selected information in which the selected operating mode is the same becomes equal to or more than a first threshold number of times, the selected operating mode from the output device after the first process is ended.

6. The method of operating the robot system of claim 5, wherein the storage device stores operation sequence information that is information relating to an operation sequence in which the series of works performed by the slave arm are defined, further comprising (E) when the first process is the automatic operation mode and the selected operating mode for the second process is the automatic operating mode, once the number of times that the first selected information is stored in the storage device becomes equal to or more than a second threshold number of times, correcting the operation sequence information so that the slave arm is operated in the automatic operation mode for the first and second processes.

7. The method of operating the robot system of claim 6, wherein the correcting (E) includes correcting the operation sequence information so that the first process and the second process are processed as a single process.

8. The method of operating the robot system of claim 6, wherein the second threshold number of times is lower than the first threshold number of times.

* * * * *